(12) United States Patent
Stedman et al.

(10) Patent No.: US 6,560,545 B2
(45) Date of Patent: May 6, 2003

(54) SYSTEM AND METHOD FOR REMOTE ANALYSIS OF SMALL ENGINE VEHICLE EMISSIONS

(75) Inventors: Donald Hugh Stedman, Denver, CO (US); Gary Allen Bishop, Louisville, CO (US)

(73) Assignee: Enviromental Systems Products, Inc., East Granby, CT (US)

( * ) Notice: Subject to any disclaimer, the term of this patent is extended or adjusted under 35 U.S.C. 154(b) by 65 days.

(21) Appl. No.: 09/740,853

(22) Filed: Dec. 21, 2000

(65) Prior Publication Data

US 2002/0010554 A1 Jan. 24, 2002

Related U.S. Application Data

(60) Provisional application No. 60/173,514, filed on Dec. 29, 1999.

(51) Int. Cl.[7] ............................................. G01N 21/00
(52) U.S. Cl. ..................................... 702/28; 250/338.5
(58) Field of Search ............................. 702/28, 23, 26, 702/27, 30, 130, 134, 183; 430/363, 56; 385/133; 359/154, 197, 208, 210, 211, 223, 318, 350, 361, 471, 534, 618, 629, 634, 664, 839, 850, 885

(56) References Cited

U.S. PATENT DOCUMENTS

| | | |
|---|---|---|
| 3,593,023 A | 7/1971 | Dodson et al. |
| 3,696,247 A | 10/1972 | McIntosh et al. |
| 3,743,426 A | 7/1973 | Steinberg |
| 3,768,908 A | 10/1973 | Zaromb |
| 3,908,167 A | 9/1975 | Hulls et al. |
| 3,957,372 A | 5/1976 | Jowett et al. |
| 3,958,122 A | 5/1976 | Jowett et al. |
| 3,973,848 A | 8/1976 | Jowett et al. |
| 4,160,373 A | 7/1979 | Fastaia et al. |
| 4,390,785 A | 6/1983 | Faulhaber et al. |
| 4,480,191 A | 10/1984 | Karpowycz |
| 4,490,043 A | 12/1984 | Cramp |
| 4,544,273 A | 10/1985 | Berndt |
| 4,560,873 A | 12/1985 | McGowan et al. |
| 4,663,961 A | 5/1987 | Nelson et al. |
| 4,719,360 A | 1/1988 | Kontani et al. |
| 4,746,218 A | 5/1988 | Lord, III |
| 4,765,961 A | 8/1988 | Schiff et al. |
| 4,795,253 A | 1/1989 | Sandridge et al. |
| 4,810,884 A | 3/1989 | Carlson |
| 4,818,705 A | 4/1989 | Schneider et al. |
| 4,829,183 A | 5/1989 | McClatchie et al. |
| 4,924,095 A | 5/1990 | Swanson, Jr. ............ 250/338.5 |
| 4,990,780 A | 2/1991 | Lee et al. |

(List continued on next page.)

OTHER PUBLICATIONS

Science—Air Pollution.
Applied Optics/vol. 10, No. 8/Aug. 1971.
Journal of the Optical Society of America/vol. 32, No. 1–12 1942.

(List continued on next page.)

Primary Examiner—Marc S. Hoff
Assistant Examiner—Edward Raymond
(74) Attorney, Agent, or Firm—Mintz Levin Cohn Ferris Glovsky and Popeo PC (57) ABSTRACT

A system and method of detecting gases in the exhaust of a moving vehicle with a small engine, such as a motorcycle or moped. The system employs a gas analyzer with a beam which makes more than two passes through a detection space. Through multiple passes through the detection space, the gas analyzer generates a signal indicative of the concentrations of one or more components of interest in the exhaust plume. The system also includes a processor for obtaining information about one or more vehicle exhaust components from the generated signal.

18 Claims, 4 Drawing Sheets

U.S. PATENT DOCUMENTS

| | | | |
|---|---|---|---|
| 4,999,498 A | 3/1991 | Hunt et al. | |
| 5,060,505 A | 10/1991 | Tury et al. | |
| 5,099,680 A | 3/1992 | Fournier et al. | |
| 5,105,651 A | 4/1992 | Gutmann | |
| 5,129,257 A | 7/1992 | Carduner et al. | |
| 5,184,017 A | 2/1993 | Tury et al. | |
| 5,210,702 A | 5/1993 | Bishop et al. | 364/496 |
| 5,246,868 A | 9/1993 | Busch et al. | |
| 5,252,828 A | 10/1993 | Kert et al. | |
| 5,306,913 A | 4/1994 | Noack et al. | |
| 5,319,199 A | 6/1994 | Stedman et al. | 250/338.5 |
| 5,327,356 A * | 7/1994 | Lang et al. | 250/338.5 |
| 5,332,901 A | 7/1994 | Eckles et al. | |
| 5,343,043 A | 8/1994 | Johnson | 250/338.5 |
| 5,371,367 A | 12/1994 | DiDomenico et al. | 250/338.5 |
| 5,373,160 A | 12/1994 | Taylor | |
| 5,386,373 A | 1/1995 | Keeler et al. | |
| 5,401,967 A | 3/1995 | Stedman et al. | 250/338.5 |
| 5,418,366 A | 5/1995 | Rubin et al. | 250/338.5 |
| 5,451,787 A | 9/1995 | Taylor | |
| 5,479,255 A * | 12/1995 | Denny et al. | 244/3.16 |
| 5,489,777 A | 2/1996 | Stedman et al. | |
| 5,498,872 A | 3/1996 | Stedman et al. | 250/338.5 |
| 5,535,314 A | 7/1996 | Alves et al. | 395/131 |
| 5,563,420 A | 10/1996 | Sulivan et al. | 250/504 |
| 5,572,424 A | 11/1996 | Kellogg et al. | |
| 5,583,765 A | 12/1996 | Kleehammer | |
| 5,589,629 A | 12/1996 | Quinn | |
| 5,591,975 A | 1/1997 | Jack et al. | 250/338.5 |
| 5,621,166 A | 4/1997 | Butler | |
| 5,644,133 A | 7/1997 | Didomenico et al. | 250/338.5 |
| 5,693,872 A | 12/1997 | Quinn | |
| 5,719,396 A | 2/1998 | Jack et al. | 250/338.5 |
| 5,726,450 A | 3/1998 | Peterson et al. | 250/338.5 |
| 5,731,510 A | 3/1998 | Jones et al. | |
| 5,753,185 A | 5/1998 | Mathews et al. | |
| 5,797,682 A | 8/1998 | Kert et al. | 374/123 |
| 5,812,249 A | 9/1998 | Johnson et al. | 356/28 |
| 5,831,267 A * | 11/1998 | Jack et al. | 250/338.5 |
| 6,396,056 B1 * | 5/2002 | Lord et al. | 250/252.1 |

OTHER PUBLICATIONS

P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.

"On Road Emissions Measurement System—Specifications," Bureau of Automotive Repair, Aug. 30, 1999, Revision—J, 15 pages.

Craig S. Rendahl, "Further Analysis of Wisconsin's Remote Vehicle Emissions Sensing Feasibility Studies," "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, May 1996, 34 pages.

James D. Peterson, et al., "Find and Fix the Polluters", Chemtech, Jan. 1992, Copyright 1992 American Chemical Society, 7 pages.

RSD 1000 Operator's Manual (Preliminary), Remote Sensing Technologies, IFB No. 94019, Jun. 1993, 66 pages.

RSD—1000 Remote Sensing Device Information Package to Mr. Wolf Klassen, Department of Natural Resources, Presented by Dennis L. Smith, Feb. 24, 1993, 123 pages.

Robert D. Stephens, et al., "An Experimental Evaluation of Remote Sensing–Based Hydrocarbon Measurements: A Comparison to FID Measurements", *Journal of the Air & Waste Management Association*, vol. 46, Feb. 1996, pp. 148–158.

Donald H. Stedman, "Automobile Carbon Monoxide Emission", *Environmental Science & Technology*, vol. 23, No. 2, 1989, pp. 147–149.

Masayuki Adachi, et al., "Automotive Emission Analyses Using FTIR Spectrophotometer", Published by the Society of Automotive Engineers, SAE# 920723, pp. 820–827.

Michael D. Koplow, et al., "Characterization of On–Road Vehicle NO Emissions by Means of a TILDAS Remote Sensing Instrument", Published by the Coordinating Research Council, Published for the $7^{th}$ CRC On–Road Vehicle Emissions Workshop, Mar. 11, 1997, pp. 1–25.

Scott E. McLaren, et al., "Comparison of an Open Path UV and FTIR Spectrophotometer", Published by the Air & Waste Management Association, Published for Presentation at the $85^{th}$ Annual Meeting & Exhibition, Kansas City, Missouri, Jun. 21–26, 1992, pp. 1–10.

"Developing an Inspection/Maintenance Program for Alternatively–Fueled Vehicles", Third Interim Report Submitted to the California Bureau of Automotive Repair, Submitted by Radian Corporation, Apr. 20, 1993, 147 pages.

Iain Frederick McVey, "Development of a Remote Sensor for Mobile Source Nitric Oxide", A Thesis Presented to the Faculty of Natural Sciences, Mathematics, and Engineering, University of Denver, Nov. 1992, 111 pages.

S. P. Beaton, et al., "Emission Characteristics of Mexico City Vehicles", *Journal of the Air & Waste Management Association*, vol. 42, No. 11, Nov. 1992, pp. 1424–1429.

Douglas R. Lawson, et al., "Emissions from In–Use Motor Vehicles in Los Angeles: A Pilot Study of Remote Sensing and the Inspection and Maintenance Program", *Journal of the Air & Waste Management Association*, vol. 40, No. 8, Aug. 1990, pp. 1096–1105.

Yi Zhang, et al., "Enhancement of Remote Sensing for Mobile Source Nitric Oxide", *Journal of the Air & Waste Management Association*, vol. 46, Jan. 1996, pp. 25–29.

Donald H. Stedman, et al., "Evaluation of a Remote Sensor for Mobile Source CO Emissions", U.S. Environmental Protection Agency, CR–815778–01–0, Report No. EPA/600/4–90/032, Jan. 1991, 90 pages.

James Butler, et al., "Factors Affecting the NDIR Measurement of Exhaust Hydrocarbons", Published by the Coordinating Research Council, Published for the CRC $5^{th}$ On–Road Vehicle Emissions Workshop, 1995, 16 pages.

Scott E. McLaren, et al., "Flux Measurements Using Simultaneous Long Path Ultraviolet and Infrared Spectroscopy", Published by the Air & Waste Management Association, Published for Presentation at the $83^{rd}$ Annual Meeting & Exhibition, Pittsburgh, Pennsylvania, Jun. 24–29, 1990, 7 pages.

Gary A. Bishop, et al., "Infrared Emission and Remote Sensing", *Journal of the Air & Waste Management Association*, vol. 42, No. 5, May 1992, pp. 695–697.

Hakan Axelsson, et al., "Measurement of Aromatic Hydrocarbons with the DOAS Technique", *Applied Spectroscopy*, vol. 49, No. 9, 1995, pp. 1254–1260.

Gary A. Bishop, et al., "Method Comparisons of Vehicle Emissions Measurements in the Fort McHenry and Tuscarora Mountain Tunnels", *Atmospheric Environment*, vol. 30, No. 12, 1996, pp. 2307–2316.

Donald H. Stedman, et al., "NOx Data by Remote Sensing", Published by the Coordinating Research Council, Published for the 5$^{th}$ CRC On–Road Vehicle Emissions Workshop, Apr. 3–5, 1995, 16 pages.

Donald H. Stedman, et al., "On–Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE–AQ–91/14, Oct. 1991, pp. 1–70.

Gary A. Bishop, et al., "On–Road Carbon Monoxide Emission Measurement Comparisons for the 1988–1989 Colorado Oxy–Fuels Program", *Environmental Science & Technology*, vol. 24, No. 6, 1990, pp. 843–847.

Donald H. Stedman, et al., "On–Road CO Remote Sensing in the Los Angeles Basin", Final Report Prepared for the Research Division, California Air Resources Board, Submitted by University of Denver Chemistry Department, Aug. 1991, Contract No. A932–189, 70 pages.

Scott McLaren, "Open Path Spectrometers for Atmospheric Monitoring", A Dissertation Presented to the Faculty of Natural Sciences, Mathematics and Engineering, Nov. 1995, 170 pages.

Carol E. Lyons, et al., "Remote Sensing Enhanced Motor Vehicle Emissions Control for Pollution Reduction in the Chicago Metropolitan Area: Siting and Issue Analysis", Final Report Prepared by University of Denver Atmospheric Science Center, Prepared for Illinois Department of Energy and Natural Resources, Office of Research and Planning, Illinois Contract AQ 30, Project 90/009, Report No. ILENR/RE–AQ–91/15, Oct. 1991, pp. 1–65.

Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.

Brett C. Singer, et al., "Scaling of Infrared Remote Sensor Hydrocarbon Measurements for Motor Vehicle Emission Inventory Calculations", *Environmental Science & Technology*, vol. 32, No. 21, 1998, pp. 3241–3248.

Lucian W. Chaney, "The Remote Measurement of Traffic Generated Carbon Monoxide", *Journal of the Air Pollution Control Association*, vol. 33, No. 3, Mar. 1983, pp. 220–222.

Jose Luis Jimenez–Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.

"Vehicle Inspection Instrumentation", Published by the Lockheed Missles and Space co., Inc., Report No. ARB–R–643–73–26, Jun. 30, 1973, 99 pages.

John E. Sigsby, Jr., et al., "Volatile Organic Compound Emissions from 46 In–Use Passenger Cars", *Environmental Science & Technology*, vol. 21, No. 5, 1987, pp. 466–475.

Yi Zhang, et al., "Worldwide On–Road Vehicle Exhaust Emissions Study by Remote Sensing", *Environmental Science & Technology*, vol. 29, No. 9, 1995, pp. 2286–2294.

Technical Proposal—"Vehicle Inspection Instrumentation", submitted to California Air Resources Board; Sep. 1, 1971, Lockheed Palo Alto Research Laboratory, Lockheed Missles & Space Company—A Group Division of Lockheed Aircraft Corporation, Palo Alto, California.

Hoshizaki, et al., Final Report—"Vehicle Inspection Instrumentation"; submitted to California Air Resources Board, Jun. 1973, Lockheed Palo Alto Research Laboratory, Lockheed Missiles & Space Company—A Group Division of Lockheed Aircraft Corporation, Palo Alto, California.

http://www.epa.gov/otag/15–remot.htm; "Remote Sensing: A Supplemental Tool for Vehicle Emission Control," Aug. 1993, EPA 400–F–92–017, Fact Sheet OMS–15; 4 pages.

Lucien W. Chaney, "The Remote Measurement of Traffic Generated Carbon Monoxide, APCA Note–Book," Journal of the Air Pollution Association; Copyright 1983, 3 pages.

Paul Stockwell, "Tunable Diode Laser Systems Break New Ground in Water Vapour Analysis"; IMA Ltd., Unit Newall Hall Park, Otley, West Yorkshire, United Kingdom; [undated]; 8 pages.

Mark G. Allen, "Diode Laser Absorption Sensors for Gas Dynamic and Combustion Flows," Copyright 1998 Measurement Science and Technology 9; 61 pages.

Kerry L. Swayne, "Infrared Remote Sensing of On–Road Motor Vehicle Emissions in Washington State," Mar., 1999, Air Quality Program, Washington State Department of Ecology, Washington; Publication #99–204, 20 pages.

Gary A. Bishop, et al., "IR Long–Path Photometry: A Remote Sensing Tool for Automobile Emissions," 1989; reprinted from Analytical Chemistry, 61. 671A; 1989; 6 pages.

Gary A. Bishop, et al., "Oxygenated Fuels, A Remote Sensing Evaluation," SAE Technical Paper Series; Copyright 1989 Society of Automotive Engineers, Inc.; 7 pages.

Robert D. Stephens, "Remote Sensing Data and a Potential Model of Vehicle Exhaust Emissions," Nov. 1994, vol. 44, Journal of Air & Waste Management Association, pp. 1284–1292.

"An Analysis of On–Road Remote Sensing as a Tool for Automobile Emissions Control," Final Report Prepared by University of Denver Chemistry Department, Colorado, Mar. 1990; 174 pages; prepared for Illinois Department of Energy and Natural Resources.

Robert D. Stephens, et al., "Remote Sensing Measurements of In–Use Vehicle Carbon Monoxide and Hydrocarbon Exhaust Emissions," Environmental Science Department, Michigan, to be presented to Society of Automotive Engineers Government/Industry Meeting, Washington, D.C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug. 28, 1990, 30 pages; prepared by Sierra Research, Inc., California.

Robert D. Stephens, et al., "Remote Sensing Measurements of Carbon Monoxide Emissions from On–Road Vehicles," Copyright Jan. 1991, Air & Waste Management Association, vol. 42, No. 1, pp. 39–46.

Donald H. Stedman, et al., "Remote Sensing of On–Road Vehicle Emissions," Final Report to Coordinating Research Council, The University of Denver, Jan. 6, 1992, 21 pages.

Peter Popp, et al., "Development of a High–Speed Ultraviolet Spectrophotometer Capable of Real–Time NO and Aromatic Hydrocarbon Detection in Vehicle Exhaust," Department of Chemistry, University of Denver, Colorado, Prepared for Proceedings of the 7$^{th}$ CRC On–Road Vehicle Emissions Workshop, San Diego, California, Apr. 9–11, 1997; 10 pages.

John DiDomenico, et al., "Preliminary Results from Cold Start Sensor Testing," Presented to 7$^{th}$ CRC On–Road Vehicle Emissions Workshop, San Diego, California Apr. 9–11, 1997; 1 page.

Gary A. Bishop, et al., "Enhancements of Remote Sensing for Vehicle Emissions in Tunnels," Air & Waste Management Association, vol. 44, Feb. 1994, pp. 169–175.

Paul Leonard Guenther, "Contributions to On–Road Remote Sensing of Automobile Exhaust," A Thesis Presented to the Faculty of Natural Sciences, Mathematics, and Engineering, University of Denver, Jun. 1992, 95 pages.

Donald H. Stedman, et al., "On–Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On–Road Emissions Measurement Systems Services," Prepared by Parsons Engineering Science, Inc., Pasadena, California, Sep. 1995.

"Proposal/Quote for Unstaffed On–Road Emissions Measurement Systems Services" in response to Phase IV—RFQ #94/95–003, prepared by Remote Sensing Technologies, Inc. delivered to Department of Consumer Affairs, Bureau of Automotive Repair, Sacramento, California, Sep. 1, 1995.

Steven H. Cadle, et al., "Measurement of Exhaust Particulate Matter Emissions from In–Use Light–Duty Motor Vehicles in the Denver, Colorado Area," Final Report prepared for Coordinating Research Council, Atlanta, Georgia, Dec. 9, 1997, prepared by General Motors R&D Center, Michigan; 20 pages.

Steven H. Cadle, et al., "Measurement of Exhaust Particulate Matter Emissions from In–Use Light–Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.

Robert D. Stephens, et al., "Remote Sensing of Carbon Monoxide Emissions from On–Road Vehicles," Environmental Science Department, General Motors Research Laboratories, Michigan for presentation to Air and Waste Management Association, NC, May 1, 1990, 46 pages.

"Description and Documentation for Interim Vehicle Clean Screening Credit Utility," Draft Report, United States Environmental Protection Agency, May 1998, 40 pages.

David S. E. Petherick, "Ontario's Indoor, Controlled–Mode Remote Sensing I/M Prescreen Concept," Ministry of Transportation of Ontario, Copyright 1996 Society of Automotive Engineers, Inc., 9 pages.

* cited by examiner

SYSTEM AND METHOD FOR REMOTE ANALYSIS OF SMALL ENGINE VEHICLE EMISSIONS

RELATED APPLICATIONS

This application is a conversion of the U.S. provisional application Ser. No. 60/173,514, entitled "SYSTEM AND METHOD FOR REMOTE ANALYSIS OF SMALL ENGINE VEHICLE EMISSIONS," filed on Dec. 29, 1999.

FIELD OF THE INVENTION

The invention relates to a system and method for remote analysis of emissions from vehicles with small engines, such as motorcycles.

BACKGROUND OF THE INVENTION

Internal combustion engines produce gaseous by-products during operation. Many of these gaseous by-products pollute the environment and, in high concentrations, can be extremely harmful. The cumulative effect of these pollutants, especially from automobiles and other vehicles, has had a significant impact on air quality and ozone depletion throughout the world.

In order to curb vehicle emissions, many states have instituted Inspection and Maintenance (IM) programs. Some IM programs include periodic inspections conducted at state run facilities. These inspections involve operating the vehicle through a series of accelerations, decelerations, stops, and starts on a chassis dynamometer and collecting the vehicle's emissions in an analyzer. These inspections take time and are inconvenient for vehicle owners.

To this end, remote sensing systems have been under development for many years. For example, U.S. Pat. No. 5,210,702 discloses a system for remotely detecting carbon monoxide and carbon dioxide levels in vehicle emissions. The system used an infrared (IR) source to project a collimated beam of IR radiation through the exhaust plume of a passing vehicle. Optical apparatus was used to separate various wavelengths of the beam and direct them to particular photodetectors. Each photodetector generated an electrical signal based on the presence or absence of light of a specified wavelength. The electrical data was fed into a computer which is used to calculate and compare the ratios of carbon monoxide and carbon dioxide exhaust components. From those ratios, high emitting vehicles were identified. These ratios could also be put into a series of equations based on the stoichiometric relationships between the exhaust components which are used to compute the concentrations which would be observed by a tailpipe probe (corrected for water and any excess air).

Other methods of determining emission concentrations using remote optical gas analyzers were also attempted. One method, disclosed in U.S. Pat. No. 4,924,095, used multiple beam paths to sample a cross-sectional "slice" of the exhaust plume. The volume of the slice was determined and used to calculate an absolute concentration of one or more exhaust components. Such a system proved inaccurate and unworkable in practice due to irregular dispersion of the exhaust plume and significant difficulties in calculating the volume of the exhaust plume.

Remote vehicle emission testing systems have undergone many improvements since originally disclosed. Some examples include: linked video surveillance of the vehicle whose emissions were to be analyzed and license plate readers to actually "read" the license plate; the combination of UV and IR radiation sources for detectors with CO, $CO_2$, $NO_x$, water, and hydrocarbon (HC) detector channels; and various optical arrangements effecting beam splitting, beam paths, filtering, and time multiplexing.

While cars and trucks are the largest source of polluting vehicle emissions, vehicles with smaller engines, such as motorcycles, mopeds, and other small motorized vehicles may also contribute to the accumulation of pollutants in urban areas. Because the engines of small motorized vehicles typically generate considerably smaller and less dense exhaust plumes, present remote sensing systems for cars and trucks may have difficulty distinguishing exhaust readings for small motorized vehicles from background noise. For example, a 50 cc moped produces an exhaust plume ten to twenty times less than that of a small car. Further, the spatial location of small engine exhaust plumes can be critical to successful remote sensing due to their small size and rapid dispersion. Due to the variability in the height of motorcycle exhaust outlets, a motorcycle exhaust plume may occur anywhere between 6 in. and 3 ft. above the ground. Present remote sensing systems may have difficulty targeting the exhaust plume of vehicles with small engines and variable height exhaust outlets.

These and other drawbacks of present remote emission sensing systems are overcome by one or more of the various preferred embodiments of the invention.

SUMMARY OF THE INVENTION

It is an object of the present invention to provide a system and method for detecting and measuring the relative concentrations of gases in the exhaust of moving vehicles with small engines.

This and other objects of the present invention may be achieved by a system for detecting components of the exhaust of moving vehicles. The system of the invention uses more than two beam passes through a detection space in order to generate a signal of sufficient magnitude to overcome the ambient noise in the detection space. Concentrations of one or more exhaust components may be calculated based on a ratio technique in order to render concentrations of one or more exhaust components independent of the absolute magnitude of the detector signal. The system includes a radiation source for producing a beam, optics for guiding the beam through the detection space, and a detector for receiving the beam and generating at least one signal indicative of the absorption of the beam in a wavelength band corresponding to one or more vehicle exhaust components. The system also includes a processor for obtaining information about one or more vehicle exhaust components from the generated signal or signals.

The present invention also relates to a method of detecting components in the exhaust of a moving vehicle. The method involves directing radiation through more than two passes through a detection space to a detector whereby the radiation passes through an exhaust plume located in the detection space. The next step is to generate at least one signal responsive to the radiation which passed through the exhaust plume. The at least one signal from the detector may be used to compute a ratio of the amounts of exhaust components. The ratio may be used to provide information about the emissions of a particular vehicle.

Other features and advantages of the present invention will be apparent to one of ordinary skill in the art upon reviewing the detailed description of the present invention.

DETAILED DESCRIPTION OF THE PREFERRED EMBODIMENTS

Figure 1:
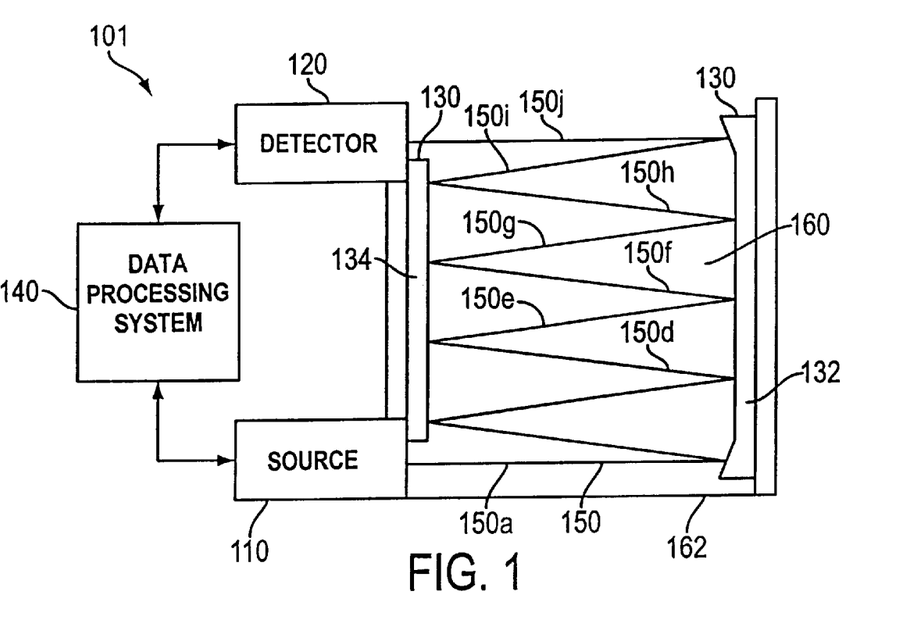
FIG. 1 is a schematic diagram of an emission testing system according to one embodiment of the invention.

With reference to the drawing figures generally, and particularly to FIG. 1, a system for detecting components of the exhaust of a moving vehicle is shown. Analyzer 101 may comprise source 110, detector 120, optics 130, and data processing system 140. Source 110 may generate a beam 150. Beam 150 may be projected from source 110 to follow a predetermined path as directed by optics 130. Optics 130 may be a system of interrelated lenses, reflectors, splitters, filters, or other optical devices for manipulating or directing radiation. Optics 130 direct beam 150 through multiple passes across detection space 160 before directing beam 150 to detector 120. Detector 120 generates a signal based on the wavelengths of radiation present in the beam. Data processing system 140 may interpret the signal from detector 120. Data processing system 140 may compute the concentration of one or more components of the vehicle exhaust or may compute ratios indicative of the relative concentrations of two or more exhaust components.

Analyzer 101 may be provided in a stationary or mobile vehicle testing lane. Gas analyzer 101 is preferably positioned such that beam 150 makes a plurality of passes through at least a portion of a passing vehicle's exhaust plume. A plurality of passes may be necessary, in some case, to provide an adequate signal, relative to ambient noise, for determining the relative amounts of compounds present in small quantities in vehicle exhaust, such as CO, $NO_x$, hydrocarbons, and other minor exhaust components. The signal returned by detector 120 may be compared to carbon dioxide, which is typically present in relatively large quantities in vehicle exhaust. In one embodiment, the ratio of one or more exhaust components may be compared to a predetermined threshold for determining whether the vehicle is a high emitter of that component. In another embodiment, data processing system 140 may calculate relative concentrations of one or more exhaust components based on the signals from the detector. The relative gas concentrations may be compared against predetermined emission standards, manually or automatically, and high emitting vehicles can be recognized in this manner.

In one embodiment, a highway, off ramp, parking lot, or other driving surface may be used as a vehicle testing lane for analyzer 101. Analyzer 101 may be set up so that beam 150 crosses a portion of the space above the driving surface substantially orthogonal or perpendicular to vehicle's direction of travel. When a vehicle's exhaust plume enters the path of beam 150, signals from the detector 120 may be used by data processing system 140 to compute the relative amounts of one or more exhaust gases.

Analyzer 101 may be permanently or temporarily installed in one or more equipment housings on either side of a vehicle path. In one embodiment, source 110, detector 120, data processing means 140, and some of optics 130 may be installed in a housing on one side of a highway and other optics 130 may be installed on the opposite side of the highway. In another embodiment, components may be installed in a plurality of housings. Preferably, at least the source 110 is contained in a housing which serves to at least partially insulate source 110 from ambient conditions in order to maintain a substantially constant temperature.

Source 110 at components may be connected by appropriate connectors, such as wires or a wireless signal transfer system. In another embodiment, some components may be housed in a vehicle, such as a van, to allow easy transportation and redeployment. In one embodiment, analyzer 101 may be mounted on a mobile structure, such as a trailer. A portion of the mobile structure may be a driving surface, preferably an inclined surface.

Source 110 produces beam 150. Beam 150 may be an optical beam of any wavelength of radiation useful in absorption spectroscopy. Source 110 may be any source for generating radiation of the wavelength or wavelengths desired. In one embodiment, beam 150 may comprise ultraviolet and infrared radiation of wavelengths specific to the absorption bands of exhaust components such as $CO_2$, CO, $NO_x$, water, hydrocarbons, or other exhaust components. Source 110 may comprise an ultraviolet source and/or an infrared source. Beam 150 may be collimated. Source 110 may produce a collimated beam or may comprise optics for collimating uncollimated radiation produced within source 110. Source 110 may produce individual beams of a plurality of predetermined wavelengths and may use optics to direct the individual beams into beam 150. Source 110 may produce a wide range of wavelengths which include the specified wavelengths for exhaust components. Multiple sources may be used.

Detector 120 may receive beam 150 and generate a signal indicative of the wavelengths received. In one embodiment, detector 120 comprises one or more sensors recognizing a particular wavelength or range of wavelengths. Detector 120 may comprise optics for splitting, filtering, and directing beam 150 or a portion of beam 150 to the sensors. These detector optics may comprise an optical mechanism for time multiplexing incoming beam 150. The sensors may generate a signal indicative of the existence and/or intensity of the radiation of the wavelength the sensor receives. Sensors may themselves be sensitive to specific wavelengths or optics, or splitters and filters may be used to direct specific wavelengths to sensors of general sensitivity. Detector 120 may include an array of sensors disposed on a microchip. Detector 120 may be a conventional spectrometer. Multiple detectors may also be used.

In one embodiment, Detector 120 is positioned above source 110 on the same side of detection space 160. Detector 120 may be spaced vertically above driving surface 162 or source 110 may be positioned proximate to driving surface 162. Detector 120 and source 110 may be situated in other positions relative to each other, detection space 160, and driving surface 162. The specific positioning may be determined by the type of source and detector used, the configuration of the optics, and the expected position of exhaust plumes. In any given configuration of the analyzer 101, the source and detector positions may be interchangeable.

Optics 130 may direct beam 150 through multiple passes through detection space 160. In one embodiment, optics 130 may comprise paired reflectors to reflect beam 150 back and forth across detection space 160. A first reflector 132 may be positioned on one side of detection space 160 and a second reflector 134 may be positioned on the opposite side of detection space 160. Beam 150 may be emitted by source 110 toward first reflector 132. Beam 150 may reflect off of a portion of first reflector 132 toward a portion of second reflector 134. Beam 150 may then reflect off of the portion of second reflector 134 back toward first reflector 134. Beam 150 may reflect back and forth across detection space 160, from first reflector 132 to second reflector 134 one or more times before being directed to detector 120. Multiple passes of beam 150 increases the likelihood of encountering emissions from a vehicle with a small exhaust plume or for vehicles having their tailpipes at non-standard positions. Multiple passes of beam 150 may encounter an exhaust plume multiple times and may help to increase the signal to noise ratio for generating a useful detector signal.

In one embodiment, as shown in FIG. 1, beam 150 makes ten passes across detection space 160. Beam 150 makes pass 150$a$ from source 110 to first reflector 132. Beam 150 makes pass 150$b$ from first reflector 132 to second reflector 134. Beam 150 makes pass 150$c$ from second reflector 134 back to first reflector 132. Beam 150 makes passes 150$d$, 150$e$, 150$f$, 150$g$, 150$h$, and 150$i$ as it is reflected back and forth between the two reflectors 132, 134. Beam 150 makes pass 150$j$ as it travels from first reflector 132 to detector 120. In this embodiment, the detection space 160 may be defined as the area approximately between first reflector 132 and second reflector 134, above driving surface 162, and below and including the path of pass 150$j$. The vertical height and placement of the detection space may vary depending on the location of exhaust ports of the vehicles being analyzed. In a more preferred embodiment for use with motorcycles and similar vehicles, the vertical height of the detection space, as measured from driving surface 162 to the top of pass 150$j$, may be about 5 feet or less. Most preferably, the detection space begins about 6 inches off the ground and goes up to a vertical height of about three feet off the ground to thereby accommodate the various types of exhaust systems routinely encountered on vehicles with small engines. Beam 150 may make at least about 2 passes per vertical foot in one embodiment, or about 4 passes per foot in an alternative embodiment.

Data processing system 140 may be coupled to detector 120 for receiving signals from detector 120 indicative of the existence and/or intensity of the radiation received by detector 120. Data processing system 140 may also be coupled to source 110. Data processing system 140 may use signals received from detector 120 to calculate ratios of one or more exhaust components in order to compensate for dispersion of the exhaust plume. Dispersion may be caused by mixing of ambient air with the exhaust plume, by wind or other ambient conditions, or by the natural process of the exhaust plume spreading out as it leaves the exhaust system. The data processing system 140 of the present invention compensates for various forms of dispersion using the ratio technique explained herein. Data processing system 140 may use signals received from detector 120 to calculate relative concentrations of one or more components of the path of beam 150. Data processing system 140 may compare the radiation intensity at specific wavelengths produced by source 110 to the radiation intensity at specific wavelengths received by detector 120. In one embodiment, data processing system 140 may use data from multiple channels, each specific to a particular emission component, to calculate relative concentrations of exhaust species. In one embodiment, data processing system 140 may use data from a continuous range of wavelengths and extract necessary data only on the wavelength or wavelength bands of interest. Data processing system 140 may use signal data to determine the relative concentration of one or more exhaust components based on each component's detected ratio to carbon dioxide and/or information derived from the stoichiometry of fuel combustion. In one embodiment, data processing system 140 may determine the relative concentration of one or more of the following: CO, $CO_2$, HC, NO, $NO_2$ and water. Data processing system 140 may also calculate relative engine temperature and/or the opacity of the exhaust plume based on signal data. Data processing system 140 need not calculate the total volume of the exhaust plume and need not determine an absolute concentration of the carbon dioxide present in the exhaust plume in order to provide accurate and useful information about various components of the exhaust plume.

In one embodiment, data processing system 140 may be part of a computer system for controlling operation of analyzer 101 and peripheral devices. The computer system may control calibration, sampling times, frequency of sampling, timing of sampling, reference sampling, components analyzed, and other aspects of the emissions analysis. The computer system may automatically compare the calculated relative concentrations of one or more components to predetermined emission standards to identify high emitters. Peripheral devices controlled may include video cameras for recording vehicles, license plate readers or other devices for specifically identifying vehicles, devices for detecting vehicle speed and acceleration, display devices and communication devices for relaying calculations and other data, storage devices for storing calculations and other data, and other peripheral devices.

Figure 2:
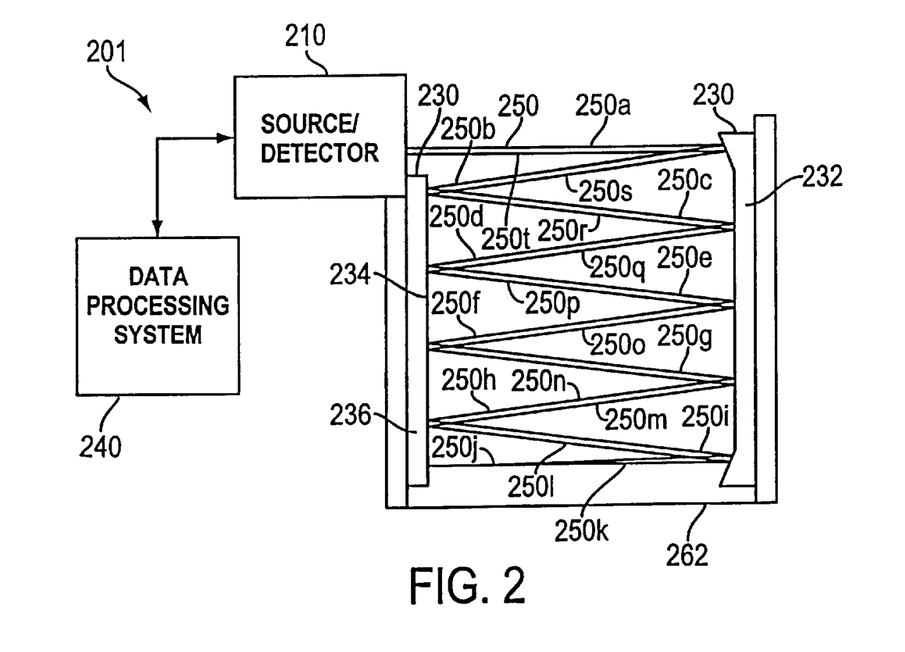
FIG. 2 is a schematic diagram of an emission testing system of a second embodiment of the invention.

FIG. 2 shows an alternate arrangement of an analyzer 201 for a system for remotely detecting components in the exhaust of a moving vehicle. In analyzer 201, a combination source/detector 210 may be positioned spaced from driving surface 262 at the top of detection space 260. Combination source/detector 210 may be a combined unit for generating and receiving beam 250. Combination source/detector 210 may otherwise operate as described above for sensor 110 and detector 120. Beam 250 is projected from source/detector 210 and guided by optics 230 through detection space 260. Optics 230 may comprise first reflector 232 on one side of detection space 260 and second reflector 234 on the other side of detection space 260. Beam 250 may be reflected back and forth between reflectors 232 and 234 in a series of passes before striking reflector portion 236. In one embodiment, beam 250 may then be reflected by reflector portion 236 back along substantially the same path between reflectors 232 and 234 to source/detector 210. In another embodiment, beam 250 may be reflected by portion 236 back along a substantially different path between reflectors 232 and 234 to source/detector 210, such as to make a crisscross pattern. Data processing system 240 may be coupled to source/detector 210 and may operate substantially as described above for data processing system 140.

In a preferred embodiment, shown in FIG. 2, beam 250 makes twenty passes through detection space 260. Beam 250 makes pass 250$a$ from source/detector 210 to first reflector 232. Beam 250 makes pass 250$b$ from first reflector 232 to second reflector 234. Beam 250 makes pass 250$c$ from second reflector 234 back to first reflector 232. Beam 250 makes passes 250$d$, 250$e$, 250$f$, 250$g$, 250$h$, and 250$i$ as it is reflected back and forth between reflectors 232 and 234. Beam 250 makes pass 250$j$ as it travels from first reflector 232 to portion 236 of second reflector 234. Portion 236 reflects beam 250 along substantially the same path beam 250 traveled between reflectors 232 and 234. Beam 250 makes passes 250$k$, 250$l$, 250$m$, 250$n$, 250$o$, 250$p$, 250$q$, 250r, and 250s as it is reflected back and forth between reflectors 232 and 234 following substantially the same path, in reverse, as passes 250j, 250i, 250h, 250g, 250f, 250e, 250d, 250c, and 250b. Beam 250 makes pass 250t from first reflector 232 to source/detector 210. The vertical height of detection space 260, as measured from driving surface 262 to the top of pass 250a, may be less than 5 feet. Beam 250 may make at least 4 passes per vertical foot.

Figure 3:
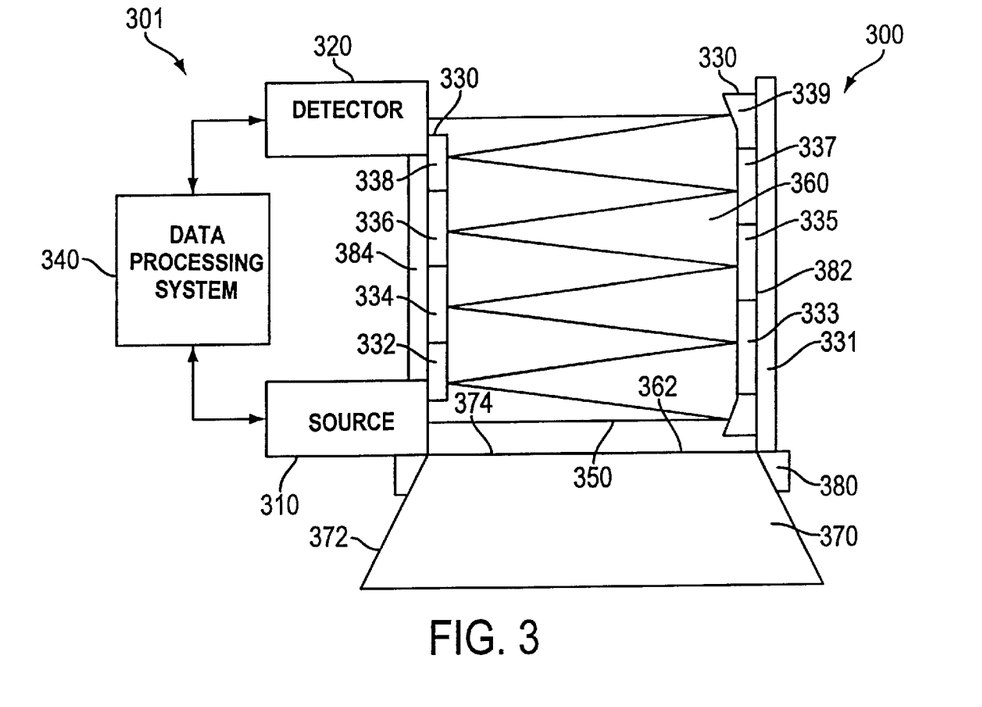
FIG. 3 is a schematic front view of a vehicle testing lane and emission testing system of a third embodiment of the invention.
Figure 4:
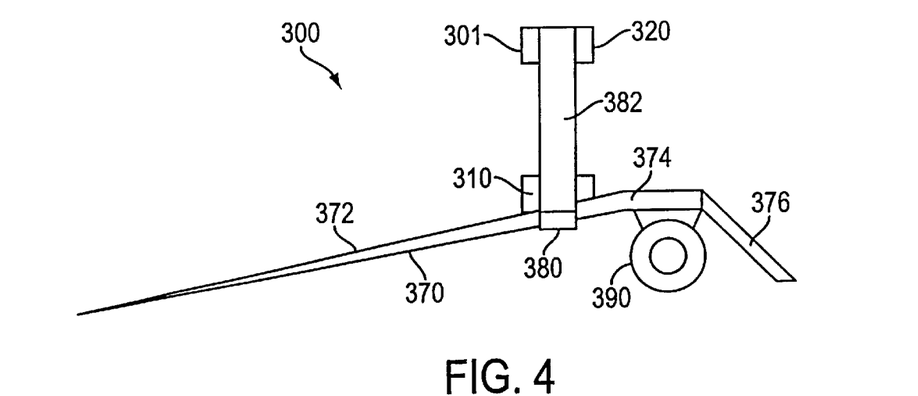
FIG. 4 is a schematic side view of the vehicle testing lane and emission testing system of FIG. 3

FIGS. 3 and 4 show an embodiment of a system for detecting components in the exhaust of a moving vehicle incorporating an analyzer 301 into a mobile vehicle testing lane 300. Mobile vehicle testing lane 300 may comprise analyzer 301, ramp 370, support structure 380, and trailer structure 390. In one embodiment, analyzer 301 may be an gas analyzer as substantially as described above for analyzer 101. Analyzer 301 may comprise source 310, detector 320, optics 330, and data processing system 340. Ramp 370 may comprise vehicle driving surface 362. Analyzer 301 may be supported by support structure 380. Analyzer 301, ramp 370, and support structure 380, may be mounted on trailer assembly 390.

Source 310 generates a beam 350. Source 310 may operate substantially as described above for source 110. Beam 350 may be projected from source 310 and follow a predetermined path as directed by optics 330.

Optics 330 may be a system of reflectors 331, 332, 333, 334, 335, 336, 337, 338, and 339. Optics 330 may direct beam 350 through multiple passes across detection space 360. Beam 350 may travel from source 310, across detection space 360, to reflector 331, from reflector 331, across detection space 360, to reflector 332, and so on between the reflectors. Reflector 339 directs beam 350 to detector 320. The width of detection space 360 measured horizontally between opposed reflectors may be a distance of 3 to 20 feet, more preferably less than 6 feet. A narrow detection space allows more passes with a shorter path length and may make testing lane 300 narrower and more easily transported. Further, a wide detection space may be unnecessary to accommodate small engine vehicles such as motorcycles, mopeds, and other small engine vehicles.

Detector 320 may receive beam 350 and generate a signal based on the wavelengths of radiation present in beam 350. Detector 320 may operate substantially as described above for detector 120.

Data processing system 340 may interpret the signal from detector 320 and compute a relative concentration of one or more components in the path of beam 350. Data processing system 340 may operate substantially as described above for data processing system 140. Alternatively, data processing system 340 may not be housed in mobile vehicle testing lane 300. In one embodiment, data processing system 340 is structurally separate from vehicle testing lane 300 but may be connected to source 310 and detector 320 by a signal transfer device. Signal transfer devices may include wires, wireless signal transfer devices, or other signal transfer devices. In one embodiment, data processing system 340 comprises a computer system for operating analyzer 300 and peripheral devices.

Ramp 370 may provide an inclined surface for guiding a vehicle through mobile vehicle testing lane 300. An inclined driving surface 362 may be provided to increase loading on a vehicle with a small engine in order to increase exhaust plume size or density or to measure emissions from the engine when under load. In one embodiment, ramp 370 may comprise an inclined portion 372 extending through detection space 362 of analyzer 301, a level portion 374 beyond detection space 362, and a declined portion to return a vehicle to ground level.

Support structure 380 may provide a frame for supporting the components of analyzer 301. Support structure 380 may provide a first vertical support 382 and a second vertical support 384. In one embodiment, vertical supports 382 and 384 may support source 310, detector 320, and optics 330. Support structure 380 may be attached to ramp 370 and/or trailer assembly 390.

Trailer assembly 390 allows mobile vehicle emissions testing lane 300 to be easily transported between testing locations. Trailer assembly 390 may comprise wheels and a coupling device for coupling testing lane 300 to a vehicle for transport. In one embodiment, testing lane 300 may have an active configuration for testing vehicle emissions and a transport configuration for transporting testing lane 300. The transport configuration may comprise folding or detaching portions of ramp 370 and/or securing portions of analyzer 301.

Figure 5:
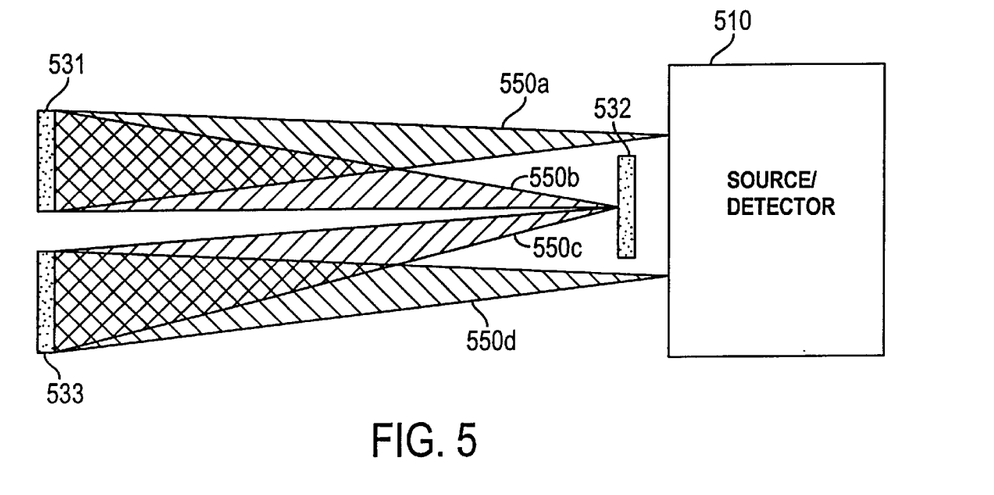
FIG. 5 is a schematic of an optical system for use in an embodiment of the invention.

FIG. 5 shows an optical configuration for use in an analyzer, such as analyzers 101, 201, and 301. FIG. 5 shows a "White" optical system. Radiation in dispersing beam 550a issues from source/detector 510. First spherical mirror 531 refocuses the radiation into converging beam 550b directed to second spherical mirror 532. Second spherical mirror 532 reflects the radiation as dispersing beam 550c directed to third spherical mirror 533. Third spherical mirror 533 refocuses the radiation into converging beam 550d. Converging beam 550d is received by source/detector 510. White optical systems may allow an extended path length with minimal loss of beam integrity. Rather than attempting to maintain a beam of parallel light along the entire path length from source to detector, White optical systems reflect and refocus the beam on multiple passes through the detection space using spherical mirrors. After the first reflection, there may theoretically be no further geometric radiation loss, only reflective loss. The resulting optical system may have the optical throughput of a short path system with the sensitivity of a long path system. The use of White optical systems may allow longer path lengths, which in turn allow a greater number of passes across a detection area by a single beam. In the laboratory, white cell optics have achieved a path length of 600 meters and may be used to achieve as many as 100 passes across a detection space.

Figure 6:
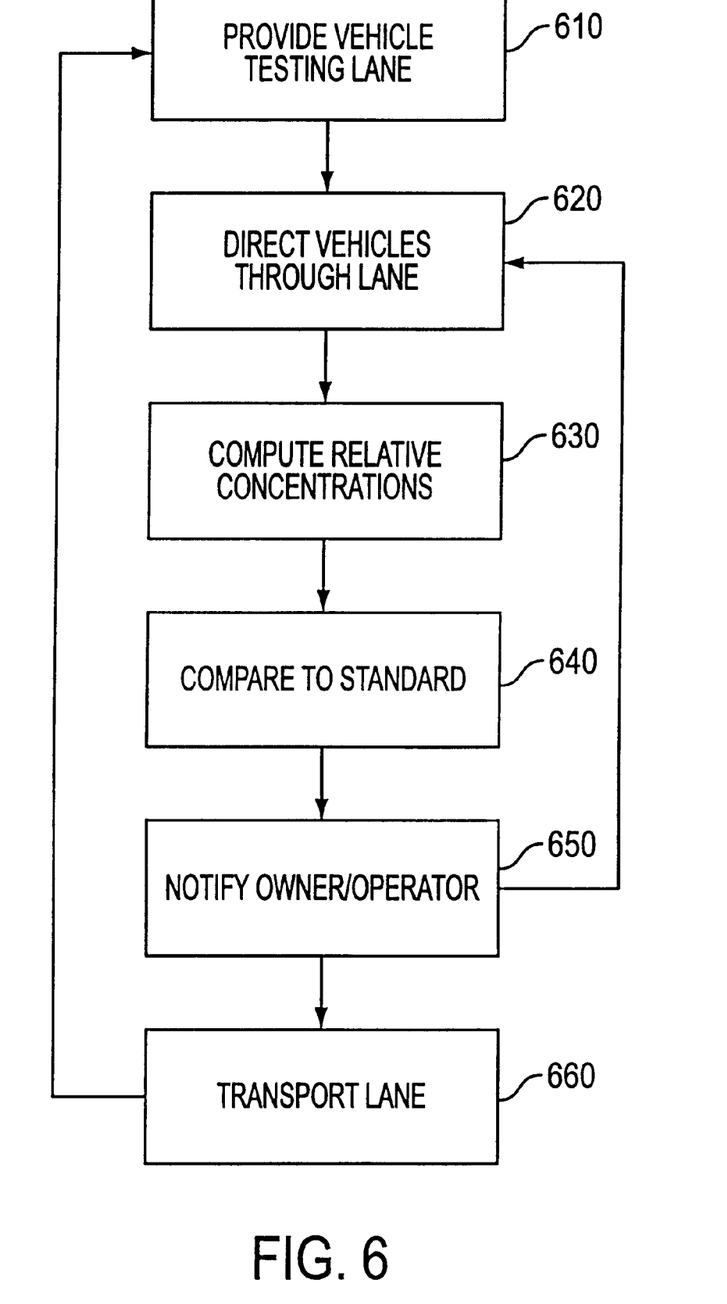
FIG. 6 is a schematic diagram of a method in accordance with the invention.

FIG. 6 shows a method of detecting gases in the exhaust of a moving vehicle. The method may be practiced using a mobile vehicle emission testing lane substantially as described for FIGS. 3 and 4 above and the testing lane may use an analyzer 101 or 201 as described for FIGS. 1 and 2 above.

In step 610, a vehicle testing lane may be provided. The testing lane may define a detection space, such as detection spaces 160, 260, or 360. The testing lane may comprise a radiation source for producing a beam, such as sources 110 or 310 or source/detector 210. The testing lane may comprise optics for guiding the beam through the detection space, such as optics 130, 230, or 330 and may use white cell optics. The testing lane may comprise a detector for receiving the beam, such as detector 120 or 320 or source/detector 210. The detector may generate an electrical signal indicative of the absorption of the beam in wavelength bands corresponding to carbon dioxide and at least one other vehicle exhaust component. The vehicle testing lane may also comprise a driving surface passing through the detection space, such as ramp 370.

In step 620, vehicles may be directed through the vehicle testing lane such that the vehicle's exhaust plume is intersected by the beam on one or more passes. The beam passing through the exhaust plume of the vehicle and being received in the detector may generate an electrical signal in the detector.

In step 630, the ratios of one or more exhaust gases may be calculated. A data processing system, such as data processing systems 140, 240, or 340, may use ratios based on the electrical signal from the detector to calculate relative concentrations of one or more exhaust components. Neither a volume of the exhaust plume, nor an absolute value of carbon dioxide in the exhaust plume need to be calculated to determine ratios or relative concentrations.

In step 640, the ratios or calculated relative concentrations may be compared to predetermined emissions standards to identify high emitters. This comparison may be made manually or may be made automatically by the data processing system.

In step 650, the owner or operator of the vehicle may be notified of the vehicle's emission profile and any need for repair or further testing based on emission standards. The agency responsible for administering an inspection and maintenance program may also be notified and emission profiles and comparisons may be stored and compiled.

In step 660, the testing lane may be transported to another testing location. All or part of the testing lane may be built into a vehicle, may be sufficiently mobile to be loaded on a vehicle, or may be mounted to a trailer assembly and trailed behind a vehicle. Some modification of the testing lane may be required for transport. Transportation allows a mobile vehicle testing lane, specifically those for small engine vehicle emissions, to be temporarily operated in a number of locations throughout an urban area. Testing may be held on days when weather encourages the use of motorcycles and mopeds and/or in areas in which such small engine vehicles are common.

This invention has been described in connection with the preferred embodiments. These embodiments are intended to be illustrative only. It will be readily appreciated by those skilled in the art that modifications may be made to these preferred embodiments without departing from the scope of the invention as defined by the appended claims.

What is claimed is:

1. A system for detecting components of the exhaust of a moving vehicle, comprising:
    a radiation source for producing radiation;
    a detector for receiving said radiation and generating at least one signal responsive to said radiation indicative of the radiation absorption of first and second vehicle exhaust components in first and second wavelength bands;
    optics for guiding said radiation through more than two passes through a detection space from said source to said detector, whereby said radiation passes through an exhaust plume of a moving vehicle in said detection space, and wherein a vertical height of the detection space is defined as the vertical distance between a horizontal surface and the location of an uppermost path of said radiation over said horizontal surface, and said optics are configured such that the radiation makes at least two passes through the detection space per foot of said vertical height; and
    a processor responsive to the at least one signal, said processor calculating a ratio of the radiation absorption of the first vehicle exhaust component to the radiation absorption of the second vehicle exhaust component to compensate for at least some dispersion of the exhaust plume.

2. The system of claim 1, wherein the processor calculates the concentration of the second vehicle exhaust component for comparison to a predetermined threshold level.

3. The system of claim 1, wherein said optics comprise a system of spherical mirrors for repeated reflection and refocusing of the radiation.

4. The system of claim 1, wherein said optics are configured such that the radiation makes at least six passes through the detection space.

5. The system of claim 1, wherein said optics are configured such that the radiation makes at least ten passes through the detection space.

6. The system of claim 1, wherein said optics are configured such that the radiation makes at least twenty passes through the detection space.

7. The system of claim 1, wherein said optics are configured such that the radiation makes at least four passes through the detection space per foot of said vertical height.

8. The system of claim 1, wherein the first vehicle exhaust component is carbon dioxide and the processor computes the concentration of a second vehicle exhaust component by comparing the absorption of the second vehicle exhaust component to the carbon dioxide absorption.

9. The system of claim 1, further comprising an inclined driving surface positioned such that a vehicle is under load as a result of having to climb the inclined driving surface when the vehicle emits an exhaust plume into the detection space.

10. The system of claim 1, further comprising a mobile structure upon which substantially all of the other components of the system are mounted for transportation to a testing site.

11. A system for detecting components of the exhaust of a moving vehicle comprising:
    a radiation source for producing radiation;
    a detector for receiving said radiation and generating at least one signal responsive to said radiation indicative of the radiation absorption of first and second vehicle exhaust components in first and second wavelength bands;
    optics for guiding said radiation through more than two passes through a detection space from said source to said detector, whereby said radiation passes through an exhaust plume of a moving vehicle in said detection space, and wherein a vertical height of the detection space is defined as the vertical distance between a horizontal surface and the location of an uppermost path of said radiation over said horizontal surface, and said optics are configured such that the radiation makes at least two passes through the detection space per foot of said vertical height; and
    a processor responsive information about the concentration of the second vehicle exhaust component using said at least one signal from the detector without calculating a volume of the exhaust plume.

12. A method of detecting gases in the exhaust of a moving vehicle comprising the steps of:
    directing radiation through more than two passes through a detection space to a detector through the use of optics, whereby the radiation passes through an exhaust plume of a vehicle located in said detection space, and wherein a vertical height of the detection space is defined as the vertical distance between a horizontal surface and the location of an uppermost path of said radiation over said horizontal surface, and said optics are configured such that the radiation makes at least two passes through the detection space per foot of said vertical height;

generating at least one signal responsive to the radiation which has passed through the vehicle exhaust plume which is indicative of the radiation absorption of first and second vehicle exhaust components in first and second wavelength bands; and obtaining information about the ratio of the second vehicle exhaust component to the first vehicle exhaust component using said at least one generated signal in order to correct for dispersion of the vehicle exhaust plume.

13. The method of claim 12, wherein the radiation makes at least four passes through the vehicle exhaust plume in the detection space.

14. The method of claim 12, wherein the radiation makes at least ten passes through the vehicle exhaust plume in the detection space.

15. The method of claim 12, wherein the concentration of at least one vehicle exhaust component is determined without calculating a volume of the exhaust plume.

16. The method of claim 12, wherein the first vehicle exhaust component is carbon dioxide and the concentration of a second vehicle exhaust component is calculated by employing equations based on fuel combustion stoichiometry and the ratio of the signal indicative of the concentration of the second exhaust component to the signal indicative of the carbon dioxide concentration.

17. The method of claim 12, wherein the vehicle exhaust plume located in the detection space is created by a vehicle which is climbing an inclined surface.

18. The method of claim 12, wherein the optics comprise a system of spherical mirrors for repeated reflection and refocusing of the radiation.

* * * * *

UNITED STATES PATENT AND TRADEMARK OFFICE
CERTIFICATE OF CORRECTION

PATENT NO. : 6,560,545 B2
DATED : May 6, 2003
INVENTOR(S) : Donald Hugh Stedman et al.

It is certified that error appears in the above-identified patent and that said Letters Patent is hereby corrected as shown below:

<u>Title page,</u>
Item [73], Assignee, change "Enviromental" to -- Environmental --.

Signed and Sealed this

Twelfth Day of August, 2003

JAMES E. ROGAN
*Director of the United States Patent and Trademark Office*